United States Patent
Bressel

(10) Patent No.: US 8,218,726 B2
(45) Date of Patent: Jul. 10, 2012

(54) IMAGING TOMOGRAPHY APPARATUS WITH BUILT-IN ENERGY STORAGE TO COVER HIGH POWER OPERATION

(75) Inventor: Wolfgang Bressel, Erlangen-Buckenhof (DE)

(73) Assignee: Siemens Aktiengesellschaft, Munich (DE)

( * ) Notice: Subject to any disclaimer, the term of this patent is extended or adjusted under 35 U.S.C. 154(b) by 160 days.

(21) Appl. No.: 12/711,392

(22) Filed: Feb. 24, 2010

(65) Prior Publication Data
US 2010/0220837 A1 Sep. 2, 2010

(30) Foreign Application Priority Data
Feb. 24, 2009 (DE) .......................... 10 2009 010 219

(51) Int. Cl.
*H05G 1/64* (2006.01)
*H05G 1/24* (2006.01)

(52) U.S. Cl. ......................................... 378/98; 378/103

(58) Field of Classification Search .................. 378/101, 378/102, 103, 117, 119, 98
See application file for complete search history.

(56) References Cited

U.S. PATENT DOCUMENTS

| | | | |
|---|---|---|---|
| 6,674,836 B2 * | 1/2004 | Harada et al. ................ | 378/107 |
| 7,197,113 B1 * | 3/2007 | Katcha et al. ................ | 378/101 |
| 2005/0281377 A1 * | 12/2005 | Heinze .......................... | 378/101 |
| 2007/0253540 A1 * | 11/2007 | Anderton et al. ............ | 378/199 |

FOREIGN PATENT DOCUMENTS
WO  WO 2008017983 A2 * 2/2008

* cited by examiner

*Primary Examiner* — Irakli Kiknadze
(74) *Attorney, Agent, or Firm* — Schiff Hardin LLP

(57) ABSTRACT

An imaging tomography apparatus has electronic components provided to operate the tomography apparatus, with at least one of the electronic components exhibiting a power consumption in high power operation that is significantly increased relative to power consumption in normal operation. The imaging tomography apparatus has an energy storage that, in high power operation, supplies the at least one electronic component with additional electrical energy to cover an energy demand due to the difference in power consumption between normal operation and high power operation. The provision of the additional electrical power in high power operation by means of the energy storage allows the modules that participate in the power supply of the at least one electronic component to be realized with lower cost. Such participating modules can be, for example: the mains connection, junction boxes with power switches (safeguards); a transformer, a rectifier, cables, slip ring brushes, slip ring tracks, etc.

8 Claims, 1 Drawing Sheet

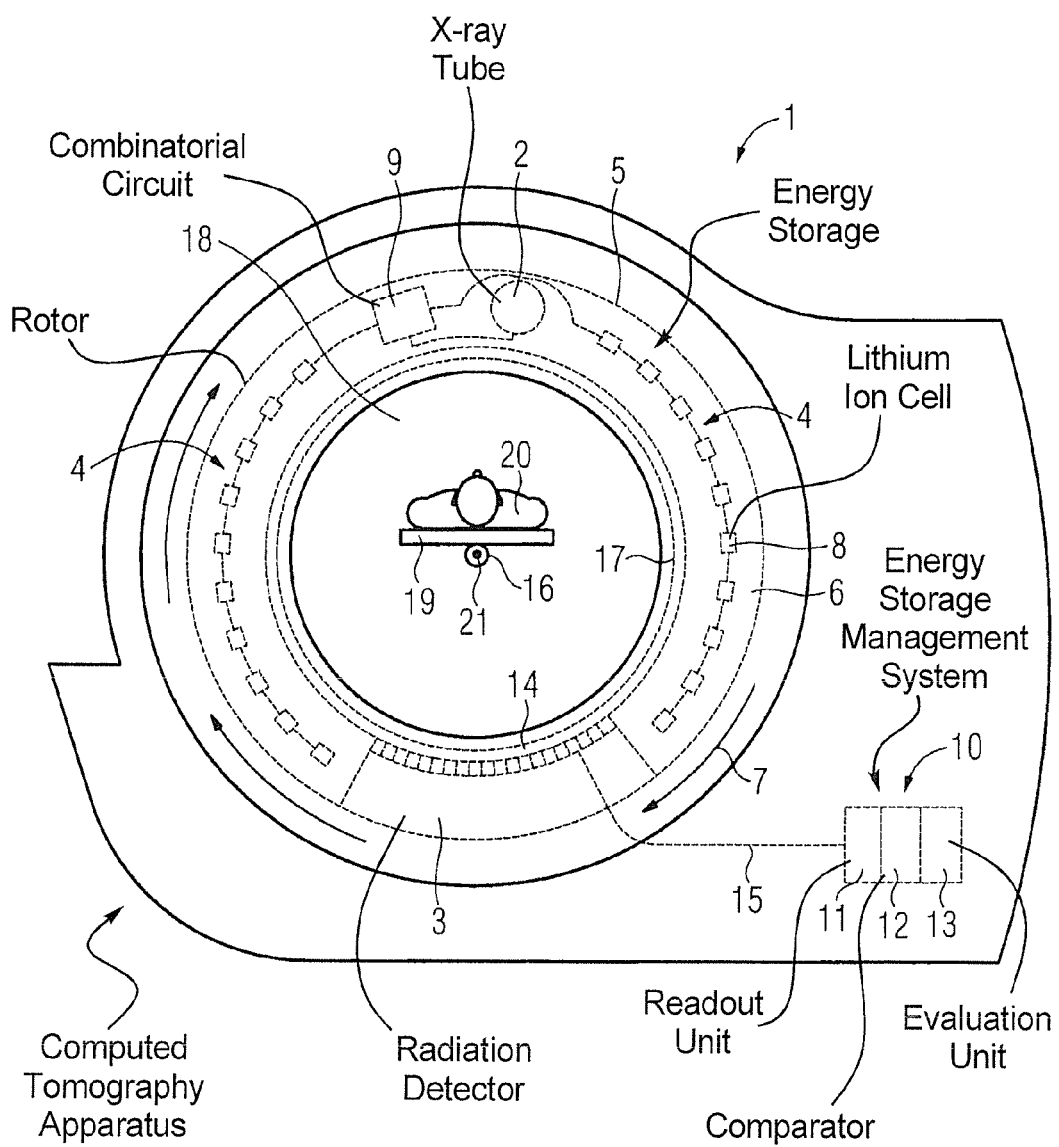

IMAGING TOMOGRAPHY APPARATUS WITH BUILT-IN ENERGY STORAGE TO COVER HIGH POWER OPERATION

BACKGROUND OF THE INVENTION

1. Field of the Invention

The invention concerns an imaging tomography apparatus with electronic components provided to operate the tomography apparatus.

2. Description of the Prior Art

Two-dimensional or three-dimensional images of an examination region of a patient are typically created with an imaging tomography apparatus for diagnostic or therapy purposes. The provision of the electrical power for the different operating modes of the tomography apparatus is an important aspect that must be taken into account in the development of the apparatus. The apparatus must always be designed for the maximum required electrical power. In an x-ray apparatus (for example a computed tomography apparatus), the difference in the required electrical power between normal operation or standby operation, and high-power operation for image acquisition, is especially large. In normal operation, a maximum average power of 5 kW is typically required to maintain the operational readiness of all electronic components, whereas a power of up to 100 kW must be provided in high power operation. The individual electrical components of such an apparatus thus exhibit very different power consumptions in the different operating modes. The electrical power required by the x-ray tube is greatest in absolute terms between the different operating modes. For example, in high-power operation in which an imaging occurs with a tube voltage value of 140 kV and a tube current value of 500 mA, a power of 70 kW must be provided solely for the x-ray tube.

It is additionally complicating that the x-ray tube is arranged on a rotor of a gantry that, in high power operation, rotates at a frequency of up to 4 Hz around a system axis of the tomography apparatus so that projections of the examination region can be acquired from a number of different projection directions. The energy required by the x-ray tube therefore must be transferred between the stationary support frame and the rotor of the gantry via slip contacts.

SUMMARY OF THE INVENTION

An object of the present invention is to provide an imaging tomography apparatus wherein the supply to the tomography apparatus with electrical energy required for high power operation is simplified.

The imaging tomography apparatus according to the invention has electronic components for operation, wherein at least one of the electronic components exhibits a power consumption in high power operation that is significantly increased relative to a power consumption in normal operation. The apparatus has an energy storage that, in high power operation, supplies the at least one electronic component with additional electrical power to cover its energy demand due to a difference in the power consumptions thereof that occur between normal operation and high power operation.

Conventionally, all modules of a tomography apparatus that participate in the electrical supply of the at least one component always had to be designed corresponding to the maximum required electrical energy.

The present invention is based on the insight that a significantly simpler and more cost-effective design of the tomography apparatus is possible by the use of an energy storage to provide the required electrical energy to cover the additional power demand. In this case the modules participating in the electrical power supply of the at least one electronic component need only be dimensioned corresponding to a maximum average power consumption in normal operation. The participating modules can be, for example: the mains connection, a junction box with power switches (safeguards), a transformer, a rectifier, cables, slip ring brushes, slip ring tracks, etc. Since, in normal operation, the maximum average power consumption normally does not exceed a value of 5 kW, commercially available modules for power supply can be used. Such modules are cost-effective, easily available and in most cases also have a smaller structural volume in comparison to modules having a more complex design. Moreover, cables with a smaller cross section and lower insulation ratings can be used.

The invention is based on the further insight that the use of an energy storage is preferred because the time spans in which high power operation is required are becoming increasingly shorter, such that the energy storage need exhibit a relatively low capacity or rating. For example, in a computed tomography apparatus, the image acquisition occurs in less than five seconds in 95% of the cases due to the high rotation speed of the gantry and due to the high z-coverage of the detector.

Because such a tomography apparatus is operated for only a very short time period in high power operation, and long time periods are present between successive examinations, the energy storage can be recharged with a low charge current. This has the result that operation of the tomography apparatus is possible using the normal mains connection at the customer, without special measures. The electrical grid (mains) at the customer therefore no longer needs to be adapted to the maximum required power in the high power operation by laying lines with greater safeguards.

In an embodiment of the invention, the at least one electronic component is an x-ray tube of an acquisition system associated with the tomography apparatus. As noted above, the x-ray tube not only exhibits the highest power consumption in the high power operation, but also for this component the difference in the required additional electrical energy between normal operation and high power operation is particularly large, such that the savings effect in the upstream modules that are responsible for electrical power supply to the x-ray tube is particularly significant. The difference in the power consumption between the normal operation and the high power operation can be up to 95 kW.

As also mentioned above, the tomography apparatus (for example in the form of a computed tomography apparatus) has a rotor mounted so as to rotate, on which rotor are arranged the x-ray tube and advantageously the energy storage. Energy transfer between the stationary support frame and the rotor is thereby simplified by means of a slip ring. Due to the reduced maximum currents, separate tracks are no longer required for the transfer of the electrical energy for the x-ray tube. The contact surfaces and carbon (graphite) brushes (and thus also the cost to maintain the slip ring) that are provided for overall power transmission are thus reduced.

In another embodiment of the invention, the energy storage is arranged on the rotor wall along a rotation direction of the rotor and is configured in a distributed manner. Since the energy storage is typically composed of a number of individual energy storage cells, a segmentation or distribution of the storage is simple to realize. In particular, with a rotationally symmetrical distribution no special measures must be taken to compensate for an out-of-balance situation.

Moreover, the energy storage can advantageously be arranged on the rotor wall so that it serves to compensate for an existing out-of-balance of the rotor. It can thus be deliberately used as a means to compensate for an out-of-balance caused by the components arranged on the rotor.

The energy storage advantageously is a battery system composed of lithium ion cells or lithium polymer cells. Lithium ion cells and lithium polymer cells exhibit a particularly high energy density, short charging times, a very low self-discharge and a high number of feasible charge cycles.

The tomography apparatus moreover advantageously has a combinatorial circuit that converts an output voltage generated by the battery system into an input voltage required by the at least one component. Such a combinatorial circuit can be flexibly adjusted to the required voltage values. A transformation between the voltage values can be implemented with such a combinatorial circuit with low power loss.

In a further embodiment, the tomography apparatus furthermore has an energy storage management system with a readout unit to determine a current charge state of the energy storage, a comparator that compares the current charge state with a charge state required for high power operation, and an evaluation unit that blocks high power operation in the event that the current charge state is too low. It is thereby ensured that high power operation can be executed completely with the present stored energy.

In addition to the computed tomography apparatus cited as an example, the imaging tomography apparatus according to the invention can naturally also be an MR apparatus, an ultrasound apparatus, a C-arm apparatus or another imaging modality. It is important that the imaging apparatus can be operated in at least two different operating modes wherein, in a high power operating mode, at least one electronic component exhibits a power consumption that is significantly increased relative to a normal operating mode.

BRIEF DESCRIPTION OF THE DRAWINGS

The single FIGURE shows, in plan view, an exemplary embodiment of a tomography apparatus according to the invention, with an energy storage.

DESCRIPTION OF THE PREFERRED EMBODIMENTS

Shown in the FIGURE is a tomography apparatus according to the invention (here a computed tomography apparatus 1) with an energy storage 4. Located inside the computed tomography apparatus 1 is a gantry with a stationary support frame 17 and a rotor 5 mounted so as to rotate around a system axis 16 in the support frame. An acquisition system, which includes electronic components in the form of an x-ray tube 2 and a radiation detector 3, is arranged on the rotor 5. The supply of the acquisition system with electrical power ensues by means of a slip ring 14 arranged between the stationary support frame 17 and the rotor 5. A patient 20 on an adjustable patient bearing device 19 is located in a tunnel opening 18. Projections from a number of different projection directions can be acquired in a spiral scan (also called a helical scan) along an examination region by rotation of the rotor 5 with simultaneous, continuous feed of the patient bearing device 19 in the direction of the system axis 16. The projection data acquired in this way by spiral scanning are transmitted to a computer (not shown) and a three-dimensional slice image is calculated therefrom.

The computed tomography apparatus 1 can be operated in normal operation and in at least one high power operation mode. In normal operation, the x-ray tube 2 requires a maximum average power of approximately 5 kW, while in high power operation a power of at most approximately 100 kW must be provided. High power operation typically occurs to generate image data of an examination region of the patient 20. The imaging can occur at, for example, a tube voltage of 140 kV and a tube current of 500 mA, which is to be equated with a power requirement of approximately 70 kW.

To cover the energy or power demand due to the difference in the power consumptions of the x-ray tube 2 that exists between normal operation and high power operation, the computer tomography apparatus 1 has an energy storage 4 with which the x-ray tube 2 is supplied with additional electrical power. Because the energy storage 4 is arranged on the rotor 5, the modules upstream of the x-ray tube 2 (for example the slip ring 14 and the cable 15) can be designed for power supply so that only the power for the normal operation need be accommodated. As noted above, the following advantages hereby result (in summary).

The modules for power supply can be produced inexpensively, are less prone to interference and require a smaller structural volume. A more compact and robust design of the entire stationary part of the computer tomography apparatus 1 can also hereby be realized.

In particular, the slip ring 14 as one of the modules can be designed without separate tracks for the electrical supply of the x-ray tube 2. Due to the reduced maximum currents, smaller contact surfaces are necessary. The wear of the carbon brushes is hereby reduced, such that a lower maintenance effort is necessary.

No special adaptations of the site installation are required at the customer for the operation of the computer tomography apparatus 1 since, due to the buffered electrical energy in the energy storage 4, the maximum power consumption of the apparatus which must be covered via the power grid in the high power operation is low.

Due to the reduced maximum currents, the cable 15 can be used with a lower cross section and lower insulation values. This has a positive effect with regard to the electromagnetic compatibility of the apparatus since, for example, the electromagnetic radiation via the slip ring 14 is reduced due to the lower currents on the tracks. Better EMC ratings according to DIN IEC-60601-1-2 are achieved overall, such that the approval of the medical apparatus is simplified.

In the present exemplary embodiment, the energy storage 4 is composed of a number of lithium ion cells 8 distributed symmetrically (with respect to their center points) relative to the rotation center 21 along the rotor wall 6. This arrangement prevents an out-of-balance situation of the rotor 5 being created by the energy storage 4. For clarity, only one lithium ion cell with one reference character 8 is provided.

The lithium ion cells 8 have a particularly high energy density and thus a low weight in comparison to the provided power. Commercially available high current lithium ion cells exhibit the following technical power parameters:

The weight per unit of power is at most 5 kW/kg in the second range, 2.5 kW/kg given a two minute operating duration and 1.25 kW/kg in long-term operation.

The weight per unit of energy is 145 Wh/kg.

The maximum charge rate is 800 W/kg in a charging time period of 10 minutes or, respectively, 2800 W/kg in 10 seconds.

For high power operation, in which imaging occurs with a tube voltage value of 140 kV and a tube current value of 500 mA, a power of 70 kW for a time duration of five seconds is required (second range). So that the energy requirement of the x-ray tube 2 can be covered by the energy storage, a battery system made up of lithium ion cells 8 with a total weight of approximately 14 kg is required. In the case of a power consumption of 100 kW, a battery system with approximately 20 kg would have to be used. It would likewise be conceivable to use a battery system with lithium polymer cells.

The energy storage 4 is connected to a combinatorial circuit 9 (likewise arranged on the rotor 5) that converts an output voltage generated by the energy storage 4 into an input voltage required by the x-ray tube 2.

The computed tomography apparatus 1 also has an energy storage management system 10 which—in this special exemplary embodiment—is arranged on the stationary part (i.e. thus on the support frame 17) of the computed tomography system 1 and is contacted with the energy storage 4 via a slip ring 14. However, it is also possible to associate the energy storage management system 10 directly with the rotor 5. The system has a readout unit 11 that determines a current charge state of the energy storage, a comparator 12 that compares the current charge state with a charge state required for the high power operation, and an evaluation unit 13 that blocks high power operation if and when the current charge state is too low. This ensures that high power operation can be implemented only if sufficient power can be provided from the energy storage 4. Moreover, the energy storage management system 10 ensures that the energy storage 4 is recharged data interface the scan pauses so that the maximum tube power is provided again in the scan.

In summary, the invention concerns an imaging tomography apparatus 1 with electronic components 2, 3 provided to operate the tomography apparatus 1, wherein at least one of the electronic components 2, 3 exhibits a power consumption in high power operation that is significantly increased relative to a power consumption in normal operation. The imaging tomography apparatus 1 has an energy storage 4 that, in high power operation, supplies at least one electronic component 2 with additional electrical energy to cover an energy demand due to a difference in the power consumption that is present between the normal operation and the high power operation. By the provision of the additional electrical power in the high power operation by means of an energy storage 4, the modules or cable 15 that participate in the power supply of the at least one electronic component 2 can be realized with lower cost. The participating modules can be, for example: the mains connection, junction boxes with power switches (safeguards), a transformer, a rectifier, cables, slip ring brushes, slip ring tracks, etc.

Although modifications and changes may be suggested by those skilled in the art, it is the intention of the inventor to embody within the patent warranted hereon all changes and modifications as reasonably and properly come within the scope of his or her contribution to the art.

I claim as my invention:

1. An imaging tomography apparatus comprising:
 a non-mobile, stationary frame having a central opening therein;
 a rotor mounted in said central opening of said non-mobile, stationary frame for rotation around a central axis proceeding through said opening;
 a plurality of power-consuming components mounted on said rotor, said plurality of components being configured to generate tomographic data and including an x-ray source and a radiation detector, said plurality of components being operable in a standby mode in which said plurality of components consume a first amount of power and in an operating mode wherein said plurality of components consume a second amount of power that is substantially higher than said first amount of power;
 a slip ring assembly located between said rotor and said non-mobile, stationary frame;
 said stationary frame comprising a power supply path configured to supply power from a power source located externally of said non-mobile stationary frame to said slip ring assembly;
 said slip ring assembly comprising dimensions and electrical properties that permit said slip ring assembly to supply power to said plurality of components that does not substantially exceed said first power level; and
 an energy storage mounted on said rotor and connected to supply power at least to said x-ray source during said operating mode.

2. An imaging tomography apparatus as claimed in claim 1 wherein said rotor exhibits a rotation direction during rotation thereof, and comprises a rotor wall, and wherein said energy storage is distributed on said rotor wall along said rotation direction.

3. An imaging tomography apparatus as claimed in claim 2 wherein said energy storage is distributed on said rotor wall to rotationally balance said rotor.

4. An imaging tomography apparatus as claimed in claim 1 wherein said energy storage comprises a battery system composed of battery cells selected from the group consisting of lithium ion cells and lithium polymer cells.

5. An imaging tomography apparatus as claimed in claim 1 comprising a combinatorial circuit that converts an output voltage generated by said energy storage into an input voltage required by said x-ray source during said operating mode.

6. An imaging tomography apparatus as claimed in claim 1 comprising an energy storage management system comprising a readout unit that determines a current charge state of said energy storage, a comparator that compares said current charge state with a charge state required for said operating mode, and an evaluation unit that blocks operation in said operating mode if said current charge state is below said charge state required for said operating mode.

7. An imaging tomography apparatus as claimed in claim 1 wherein said slip ring assembly comprises a plurality of tracks, with none of said tracks being in electrical connection with said x-ray source.

8. An imaging tomography apparatus as claimed in claim 1 wherein said first power level is 5 kV.

* * * * *